United States Patent [19]

Morin

[11] Patent Number: 5,676,008
[45] Date of Patent: Oct. 14, 1997

[54] APPARATUS AND METHOD OF FORMING NEEDLE BLANKS FROM WIRE STOCK

[75] Inventor: Donald A. Morin, Goffstown, N.H.

[73] Assignee: United States Surgical Corporation, Norwalk, Conn.

[21] Appl. No.: 590,227

[22] Filed: Jan. 23, 1996

[51] Int. Cl.[6] .............................. B21F 11/00; B21G 1/00
[52] U.S. Cl. ........................ 72/129; 72/135; 72/324; 163/1; 163/5; 140/92.2; 83/907
[58] Field of Search ...................... 72/129, 135, 324; 83/950, 907, 697; 140/92.2, 92.1; 163/1, 5

[56] References Cited

U.S. PATENT DOCUMENTS

| 581,532 | 4/1897 | Booth | 83/907 |
|---|---|---|---|
| 1,602,509 | 10/1926 | Six | 83/907 |
| 1,735,759 | 11/1929 | Hofmann et al. . | |
| 2,128,437 | 8/1938 | Stenwell | 72/129 |
| 2,623,550 | 12/1952 | Artoni | 72/129 |
| 4,051,874 | 10/1977 | Hardy | 140/92.2 |
| 4,672,734 | 6/1987 | Kawada et al. | 163/1 |
| 4,785,868 | 11/1988 | Koenig, Jr. | 163/5 |
| 5,526,666 | 6/1996 | Bogart | 163/1 |

FOREIGN PATENT DOCUMENTS

| 0650698 | 5/1995 | European Pat. Off. . | |
|---|---|---|---|
| 601235 | 8/1934 | Germany | 72/129 |
| 2947806 | 11/1979 | Germany . | |
| 592939 | 5/1959 | Italy | 72/129 |
| 123543 | 5/1988 | Japan | 163/1 |
| 281025 | 12/1991 | Japan | 163/1 |

Primary Examiner—Daniel C. Crane

[57] ABSTRACT

There is disclosed an apparatus and method for forming curved and pointed needle blanks from a coiled length of wire needle stock material. The apparatus includes an inner mandrel having a circumferential wire receiving groove and at least one longitudinally extending broach receiving channel formed in the outer surface. The apparatus also includes an outer member having an inner surface defining a bore sized to receive the inner mandrel wrapped with wire needle stock. The outer member includes at least one longitudinal broach receiving channel formed in the outer member inner surface. The outer mandrel further includes a circumferential wire receiving groove formed in the inner surface such that, when wrapped with the length of wire needle stock material, the inner mandrel is threaded into the outer member. The apparatus further includes at least one broach which is movable within the channels to cut the length of wire needle stock into curved and pointed needle blanks. The method includes wrapping a length of wire needle stock around an inner mandrel and inserting the wire wrapped mandrel within an outer member. The method further includes moving at least one broach within a longitudinal channel formed in at least one of the mandrel and outer member to cut the length of wire needle stock into needle blanks. A needle blank formed by the apparatus and method is disclosed.

18 Claims, 4 Drawing Sheets

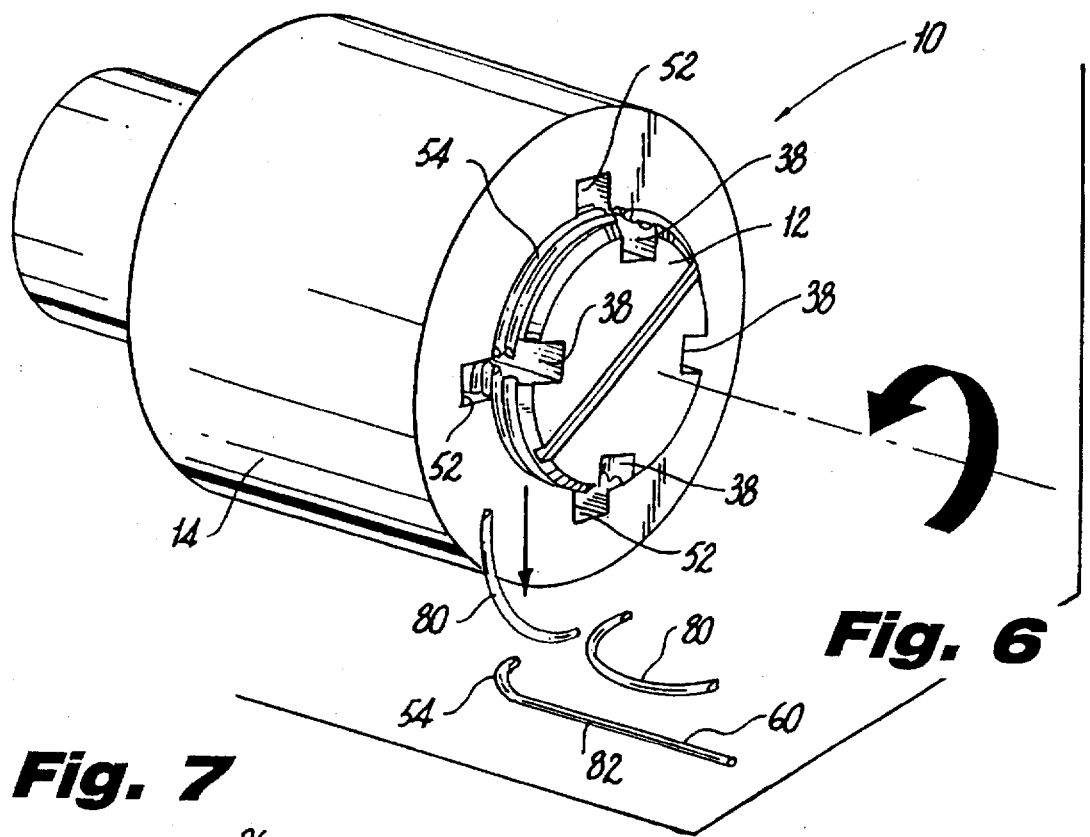
Fig. 6
Fig. 7
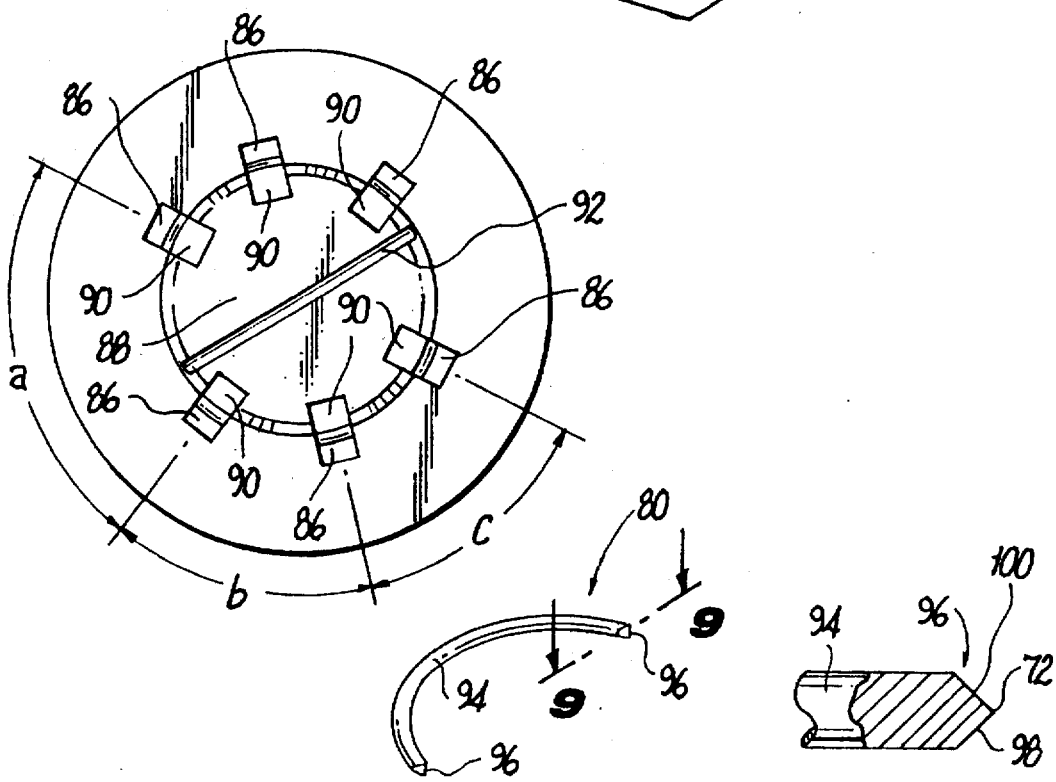
Fig. 8
Fig. 9

APPARATUS AND METHOD OF FORMING NEEDLE BLANKS FROM WIRE STOCK

BACKGROUND

1. Technical Field

This disclosure relates generally to the formation of surgical needle blanks, and more particularly, to apparatus for forming needle blanks and methods of forming curved and double pointed needle blanks from a length of wire needle stock.

2. Description of Related Art

The production of needles involves many processes and different types of machinery in order to prepare quality needles from raw stock. These varying processes and machinery become more critical in the preparation of surgical needles where the environment of intended use is in humans or animals. Some of the processes involved in the production of surgical grade needles include, inter alia, straightening wire stock, cutting needle blanks from raw stock, tapering or grinding points on one or both ends of the blank, and providing structure for receiving suture thread at an end of the blank (in the case of a single pointed needle) or at a location intermediate the ends (in the case of a double ended surgical incision member). As used herein, the term "needle blank" refers to a piece of needle stock material at various stages of completion but not fully formed into a surgical grade needle suitable for use during surgical procedures. Additionally, flat surfaces may be formed on the sides and/or top and bottom of the needle blank to facilitate grasping the needle using known surgical instrumentation.

Conventional needle processing is, in large part, a labor intensive operation requiring highly skilled labor and sophisticated machinery. Generally, extreme care must be taken to ensure that only the intended working of the needle is performed and the other parts of the needle remain undisturbed.

Certain types of surgical needles, such as, for example, double pointed and curved surgical needles, or surgical incision members, may require several processes to form the finished surgical needle. These processes may include curving and cutting needle stock to form needle blanks for subsequent processing. Later processing may include altering or refining the tip configurations and curvature radius, punching or drilling the blank to form a suture hole and notching an edge of the blank to provide a recess for engagement with corresponding engagement structure on various surgical suturing apparatus. Further, subsequent processing apparatus may be capable of handling a large number, or even a continuous flow, of needle blanks.

One disadvantage to conventional needle forming techniques is that typically only one or very few needle processing operations are performed at a time in a batch operation, such as, for example, cutting the blanks from stock, tapering the stock to form points, curving the blanks, etc.

Thus it would be desirable to have an apparatus for forming a large number of curved and pointed needle blanks, suitable for further finishing and refining, in a very short time and with a minimal amount of machinery. It further would be desirable to provide curved and pointed needles in a manner for continuous rapid delivery for subsequent processing.

SUMMARY

The disclosed surgical instrumentation relates to apparatus for forming curved needle blanks from a preformed helically wound length of wire needle stock. The apparatus generally includes a mandrel for receipt of a length of wire wrapped around an outer surface thereof and having at least one longitudinal channel formed in the outer surface, and an outer member having an inner surface defining a cavity therein. The cavity is configured and dimensioned to receive the mandrel wrapped with the length of wire. The outer member further includes at least one longitudinal channel formed in the inner surface and alignable with the mandrel channel. At least one broach is provided and is configured for insertion within at least one of the mandrel or outer member channels such that an edge of the die projects out of the channel and engages the length of wire.

Preferably the mandrel is cylindrical and the outer surface of the mandrel includes a circumferential wire receiving groove formed therein. The wire receiving groove may have a semicircular cross-section or a rectangular cross-section. Further, the wire receiving groove is preferably formed in a predetermined pitch in the outer surface of the mandrel. The mandrel may also include an anchor groove formed in one end face thereof, the anchor groove being configured to retain a portion of the length of wire. The mandrel has a mounting portion extending from one end thereof and configured for engagement with a mounting fixture.

The outer member also includes a circumferential wire receiving groove formed in the inner surface thereof. Preferably the broach includes a base portion and a wire engaging portion. The wire engaging portion includes a plurality of progressively deeper cutting teeth. There may also be provided a driver configured for engagement with the broach such that movement of the driver causes the broach to move longitudinally within one of the mandrel or outer member channels and score an edge of the wire. Preferably, the broach is affixed to the driver.

The disclosed method relates to a method of forming needle blanks from a length of wire needle stock by wrapping the length of wire needle stock around a mandrel in the circumferential groove, inserting the wire wrapped mandrel within an outer member with the wire in the outer member circumferential groove so that the wire is held between the mandrel and the outer member. The method further includes moving at least one broach within a longitudinal channel formed in at least one of the mandrel and outer member to cut the length of wire stock into needle blanks. The method may further include the step of moving a pair of broaches through opposed longitudinal channels formed in the mandrel and the outer member to cut portions of the wire needle stock into needle blanks, preferably into curved, pointed needle blanks.

There are also disclosed curved, pointed needle blanks formed on, and according to, the above described apparatus and method.

BRIEF DESCRIPTION OF THE DRAWINGS

Various embodiments are described herein with reference to the drawings, wherein:

FIG. 6 is a perspective view of the apparatus of FIG. 1 illustrating sequential unloading of the pointed curved needle blanks from between the outer member and inner mandrel;

FIG. 7 is an end view of apparatus similar to the apparatus of FIG. 1 and illustrating multiple broaching channels and various spacings between the channels;

FIG. 8 is a perspective view of a double pointed and curved needle blank formed on the apparatus of FIG. 1; and FIG. 9 is a partial cross-sectional view of the double pointed and curved needle blank taken along the line 9—9 of FIG. 8.

DESCRIPTION OF PREFERRED EMBODIMENT(S)

Figure 1:
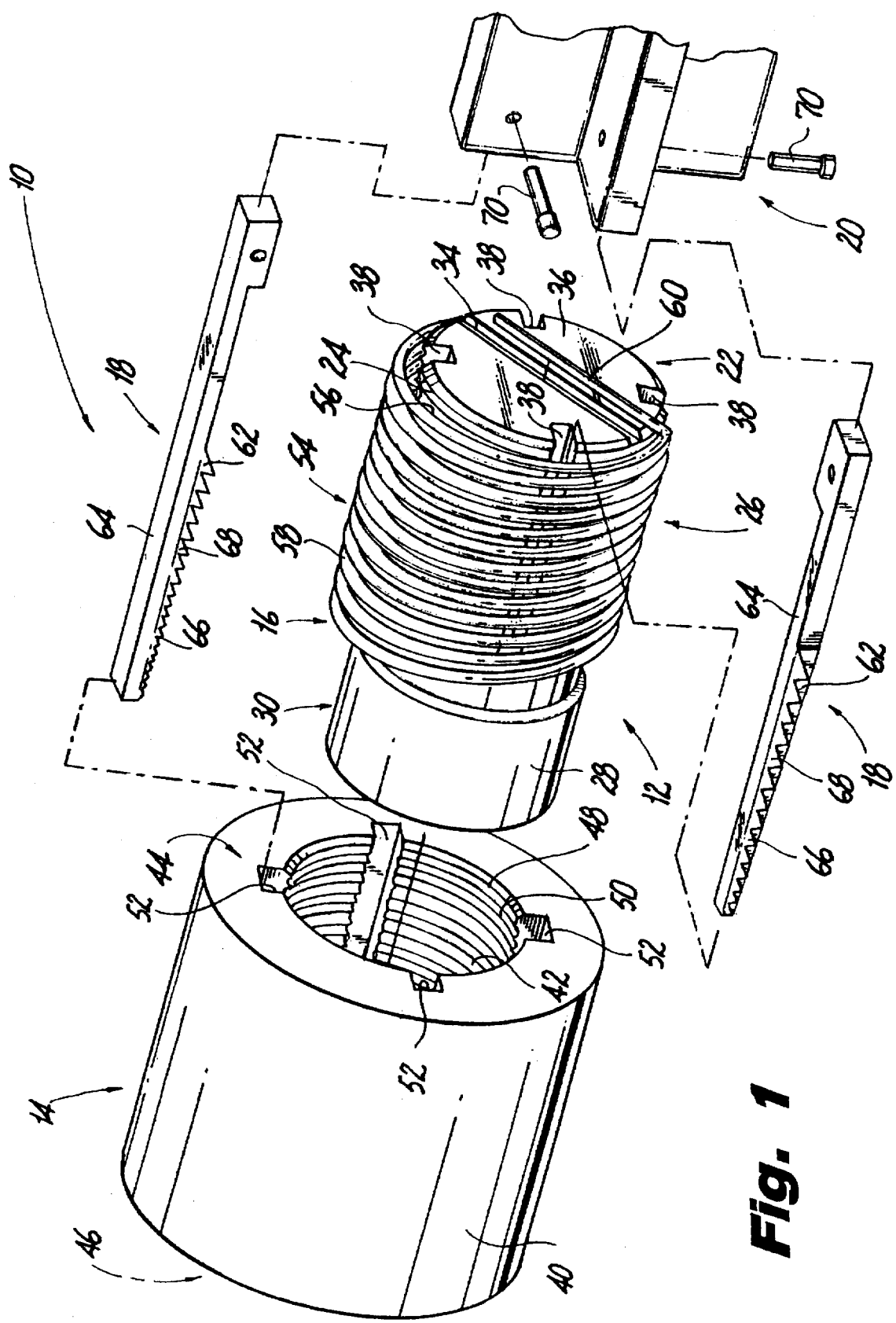
FIG. 1 is a perspective view of an apparatus for forming curved double pointed needle blanks with pans separated.

Referring to FIG. 1, there is depicted a needle forming apparatus 10 which is particularly suited to rapidly and efficiently form a large number of curved and double pointed needle blanks from a length of wire needle stock material upon passing of cutting dies or broaches. The resultant needle blanks are suitable for subsequent processing such as, for example, notching and hole drilling to form surgical incision members. While apparatus 10 is particularly suited to form curved double pointed needle bias, single pointed, straight or other types of needle blanks are also capable of being formed on apparatus 10 as described more fully hereinbelow.

Apparatus 10 generally includes an inner mandrel 12 and an outer member 14 which are dimensioned and configured to firmly hold a preformed helically coiled length of wire needle stock 16 therebetween. Apparatus 10 further includes at least one, and preferably multiple, broaches 18. Broaches 18 are movable between inner mandrel 12 and outer member 14 to cut a segment of the curved length of wire needle stock 16 at various locations, thereby forming a relatively large number of pointed needle blanks upon passing of broaches 18 therethrough. A driver 20 is provided to push or pull broaches 18 between inner mandrel 12 and outer member 14. Preferably, multiple passes of broaches 18 are performed so as to partially cut through cylindrical length of wire needle stock 16 on any given single pass. This aids in preventing stressing of the needle stock and facilitates chip removal. Of course, a single pass with the same or different broaches could be used, if desired, so as to completely cut through a segment of cylindrical length of wire needle stock 16 upon a single pass of broach 18.

To firmly hold the length of wire needle stock 16, inner mandrel 12 is configured to be insertable within outer member 14 and includes a threaded portion 22 having a circumferential wire receiving groove or thread 24 configured to receive wire needle stock 16 wound therearound in groove 24. Preferably thread 24 has a pitch on the order of approximately 25% larger than the pitch of the length of coiled wire needle stock 16. This preferred pitch is selected to separate adjacent coils of wire needle stock by about one quarter of a wire diameter in order to facilitate chip removal during broaching. It will be noted that, while thread 24 is of an even pitch, the pitch of thread 24 may be varied so as to impart various angles to segments of curved wire needle stock 16 engaged by broaches 18. Threaded portion 22 is generally formed towards a first end 26 of inner mandrel 12. Inner mandrel 12 further includes a mounting portion 28 formed towards a second end 30 and configured to be positively held by an external fixture (not shown). For double pointed surgical incision members made from wire of about 0.034 inches in diameter, groove 24 preferably has a pitch between grooves of from about 0.001 to 0.060 inches and more preferably from about 0.020 to 0.040 inches.

As noted above, inner mandrel 12 includes threaded portion 22 which is designed to firmly hold length of wire needle stock 16 wrapped therearound. In order to secure length of wire needle stock 16 to inner mandrel 12 during insertion into outer cylinder 14, and during cutting by broaches 18, an anchor slot 34 is formed at first end 26 in an end face 36 to retain a straight portion of the wire stock and prevent any movement of the wire stock relative to the inner mandrel during processing. Inner mandrel 12 further includes at least one and preferably a plurality of longitudinal channels 38 formed in threaded portion 22 which interrupt or intersect threads 24. Channels 38 are dimensioned and configured such that when broaches 18 are slid therein, a cutting portion of each broach 18 projects sufficiently to score or cut a segment of wire needle stock 16 engaged thereby. The full length of the broach preferably scores the wire needle stock approximately halfway through the wire.

Outer member 14 generally includes an outer surface 40 and an inner cavity or bore 42 which is dimensioned and configured to receive inner mandrel 12 with wire needle stock 16 wrapped therearound. It will be noted that while outer surface 40 of outer member 14 is preferably cylindrical, outer surface 40 may have various other configurations, such as, for example, rectangular, etc. in order to more easily secure outer member 14 within a mounting fixture. Bore 42 preferably extends completely through outer member 14 from a first end 44 to a second end 46 of outer member 14. Bore 42 of outer member 14 defines an inner surface 48 containing a circumferential wire receiving groove or thread 50 formed therein. Thread 50 in outer member 14 is of a substantially identical pitch to thread 24 of inner mandrel 12 in order to support and firmly hold wire needle stock 16 between thread 24 and thread 50. Outer member 14 further includes at least one and preferably a plurality of longitudinal channels 52 which are, like channels 38 in inner mandrel 12, dimensioned and configured to slidingly receive broaches 18 therein in order to cut or score a portion of wire needle stock 16. Preferably outer member 14 has a number of channels 52 equal to the number of channels 38 formed in inner mandrel 14 and radially alignable therewith so as to evenly and completely cut through wire needle stock 16 at various locations.

As noted hereinabove, inner mandrel 12 and outer member 14 include threads 24 and 50 respectively which are dimensioned and configured to firmly hold wire needle stock 16 therein. Wire needle stock 16 is preferably preformed into a helical coil potion 54 generally having a radius of curvature substantially equal to the desired radius of the finished needle blank. Coil portion 54 has an inner radial surface 56 which, when wrapped around inner mandrel 12, rests in threads 24 and is firmly held thereby. Coil portion 54 further includes an outer radial surface 58 which is engagable with threads 50 upon insertion of inner mandrel 12 within outer member 14. Thus, by preforming wire needle stock 16 with coil portion 54, needle blanks cut therefrom will be curved, preferably with the desired curvature of the finished needle. Curved wire needle stock 16 may be further formed with a straight free end portion 60 which is dimensioned to be inserted into anchor slot 34 in end face 36 of inner mandrel 12 in order to prevent movement of wire needle stock 16 relative to inner mandrel 12 upon insertion within outer member 14. Preferably, wire needle stock 16 has an outer diameter of from about 0.002 inches to 0.060 inches or more and, more preferably, from approximately 0.024 inches to about 0.044 inches. Coil portion 54 may have any desired radius corresponding to the desired needle curvature.

Figure 2:
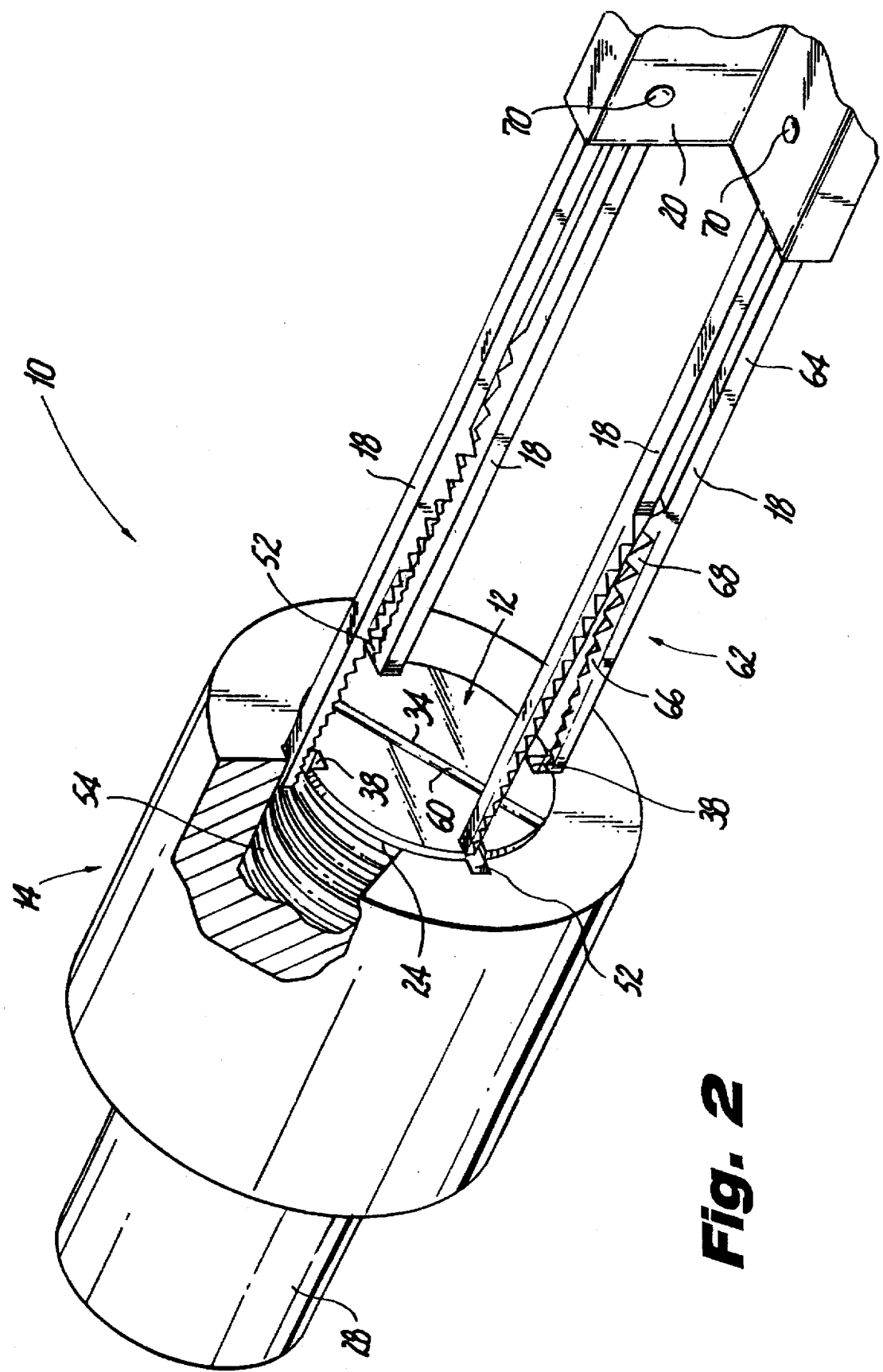
FIG. 2 is an assembled perspective view of the apparatus depicted in FIG. 1.

Referring now to FIGS. 1 and 2, and as noted hereinabove, apparatus 10 additionally includes a plurality of broaches 18 which are longitudinally slidable within channels 38 and 52 of inner mandrel 12 and outer member 14, respectively, to cut or score pointed edges in coil portion 54 in order to form double pointed and curved surgical needle blanks. Broaches 18 generally include cutting or scoring portions 62 which are configured to impart a pointed edge to segments of curved wire needle stock 16. Scoring portions 62 are affixed to base portions 64 which slide within channels 38 and 52. Preferably, cutting portions 62 include teeth, such as teeth 66 and 68, which progressively increase the depth of the cut to impart a "chisel" edge to coil portion 54, although straight cutting portions may be provided to cut flush or flat edges in coil portion 54, i.e., to form single pointed needle blanks. Cutting portions 62 and base portions 64 are further dimensioned and configured such that, when slid within a channel, such as for example, channel 52 in outer member 14, cutting portion 62 engages an edge of coil portion 54 while base portion 64 remains within channel 52 and does not contact wire portion 54. In order to move broaches 18 within the channels, broaches 18 are attached to driver 20 by means of pins 70. Broaches 18 are therefore removably engagable with driver 20.

In operation, apparatus 10 is initially assembled by threading coil portion 54 of length of wire needle stock 16 onto threads 24 of inner mandrel 12 and inserting straight free end portion 60 within anchor slot 34. Preferably, wire needle stock 16 is preformed with coil portion 54 having a radius substantially equal to that of inner mandrel 12, and thus the desired final needle blank radius, and with straight free end portion 60. Coiled length of wire needle stock 16 is threaded onto inner mandrel 12 such that an inner radial surface 56 of coil portion 54 rests within threads 24 in inner mandrel 12. Alternatively, helically coiled wire needle stock 16 may be positioned on inner mandrel 12 by taking a straight piece of wire stock and inserting a portion thereof into anchor slot 34 to form straight free end portion 60 and subsequentially wrapping the remainder of straight wire needle stock 16 around inner mandrel 12 and within the threads 24 to form coil portion 54.

In order to insert inner mandrel 12, wrapped with coiled wire needle stock 16, within outer cylinder 14, fast end 26 of inner mandrel 12 is preferably positioned at second end 46 of outer cylinder 14. Inner mandrel 12 can then be rotated relative to outer member 14 to cause outer radial surface 58 of coil portion 54 to engage threads 50 in an outer member 14. Thus inner mandrel 12 and coil portion 54, as a unit, are "threaded into" outer member 14. By rotating inner mandrel 12 into outer member 14 from end 46, coil portion 54 is further tightened about inner mandrel 12 and, as an added benefit, coil portion 54 is forced to assume the exact radius of inner mandrel 12, and, consequently, of the desired finished needle blank. Thus, inner mandrel 12 is inserted into outer member 14 without coil portion 54 unravelling from inner mandrel 12. As noted above, while threading inner mandrel 12 and wire needle stock 16 within outer member 14, coil portion 54 is prevented from moving undesirably within threads 24 and 50 by straight portion 60 disposed in anchor slot 34. Thus, as inner mandrel 12 is rotated, an outer radial surface 58 of length of wire needle stock 16 engages and is held within threads 50 in outer member 14. In this manner inner mandrel 12 and outer member 14, containing coiled length of wire needle stock 16, are assembled and ready for broaching with broaches 18.

Once wire needle stock 16 has been assembled within outer member 14 and inner mandrel 12, broaches 18 are affixed to driver 20 by means of pins 70. Broaches 18 are inserted into channels 38 and 52 alternately so as to only cut approximately half way through a segment of curved needle stock on each pass of broaches 18. After a pass, broaches 18 can be rotated and reinserted in channels 38 and 52 to finish cutting through a segment of curved cylindrical length of needle stock 16. Preferably, mounting portions 28 and outer surface 40 of inner mandrel 12 and outer member 14, respectively, are engaged by mounting fixtures to firmly hold apparatus 10 during the actual broaching or cutting operation.

Figure 3:
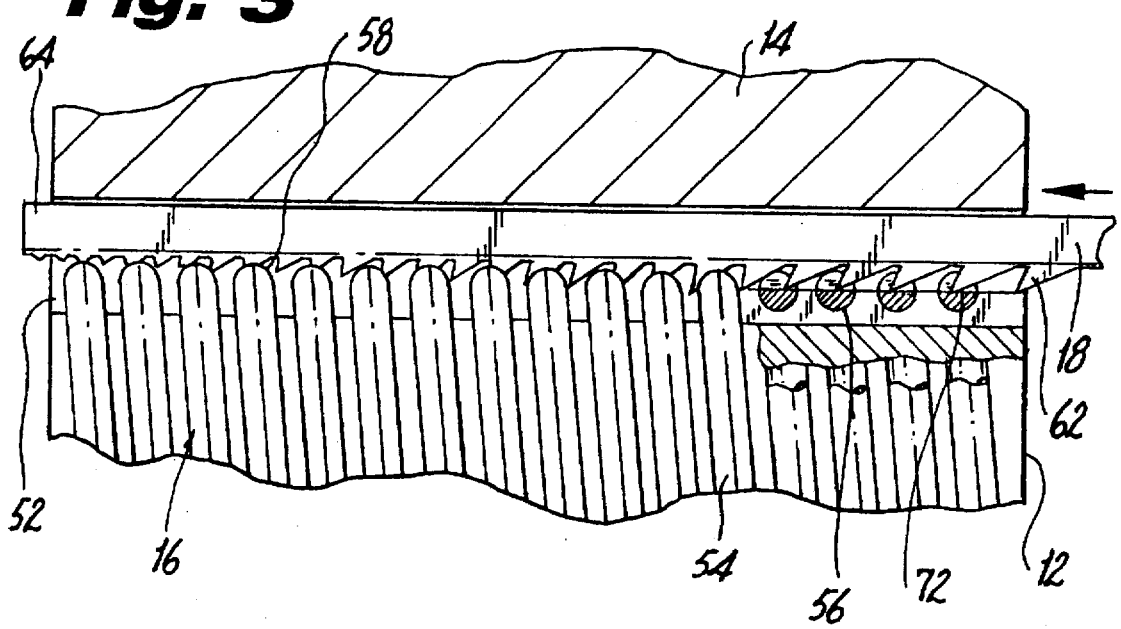
FIG. 3 is a partial cross-sectional view of the apparatus depicted in FIG. 2 showing a broach cutting the wire stock to form points.

Referring now to FIGS. 2 and 3, and as noted above, broaches 18 are longitudinally moved within channels 38 and 52 by driver 20 in order to cause cutting portions 62 to engage and cut points in coil portion 54. Referring specifically to FIG. 3, as cutting portions 62 are moved within channels 52, 38, cutting portions 62 engage coil portion 54 of length of wire needle stock 16 to cut partially through coil portion 54. Broaches 18 are then rotated to cause the opposed pairs of inner and outer facing broaches 18 to enter alternate channels 38 and 52 to cut completely through segments of curved wire needle stock 16 and form a chiseled points 72 thereon. As noted above, base portions 64 slide within channels 38, 52 such that they do not engage and damage inner or outer radial surfaces 56, 58, respectively, of coil portion 54.

Figure 4:
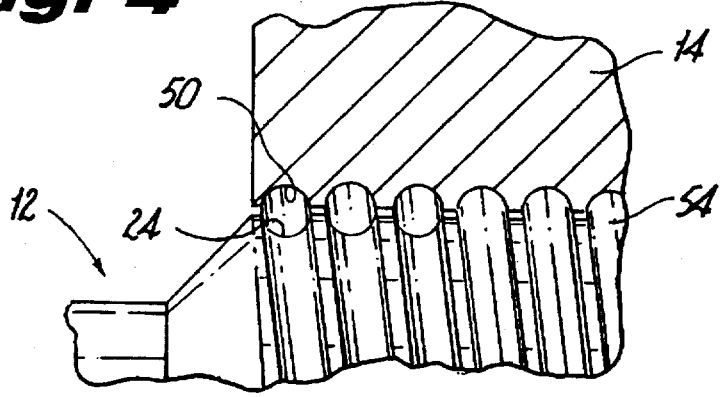
FIG. 4 is a partial cross-sectional side elevational view of the mandrel and outer member of FIG. 1.

As best illustrated in FIG. 4, inner mandrel 12 and outer member 14 are dimensioned and configured such that when coil portion 54 is threaded between inner mandrel 12 and outer member 14, threads 24 and 50 do not touch and the coils of curved cylindrical length of wire needle stock 16 are separated by approximately one-quarter of a needle diameter. As noted above, in one embodiment it is preferable to use round wire stock in order to form round and curved double chisel pointed needle blanks.

Figure 5:
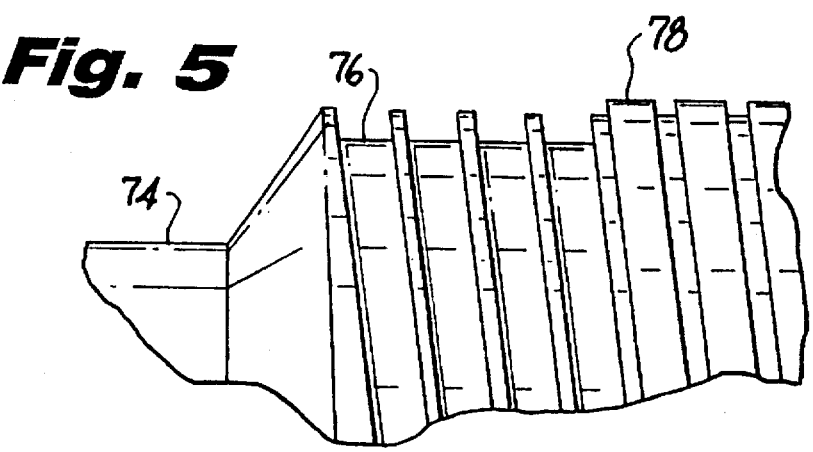
FIG. 5 is a partial side elevational view of an alternate mandrel illustrating a rectangular wire groove for receipt of rectangular wire stock.

Referring to FIG. 5, however, in certain instances it may be preferable for a surgical needle to have a rectangular cross section for enhanced strength and rigidity or tissue penetration characteristics. Thus, an alternate inner mandrel 74 may be provided having a square thread 76 therein in order to accommodate a coiled length of rectangular wire needle stock 78. When rectangular wire stock is used with apparatus 10 outer member 14 is also formed with square thread similar to thread 76. Thus, upon broaching by broaches 18, apparatus 10 is capable of forming curved rectangular bodied needles having chisel points at either end. Further, while inner mandrel 12 and outer member 14 are preferably cylindrical to form curved needle blanks, both inner mandrel 12 and at least inner surface 52 of outer member 14 may have other shapes, such as, for example, rectangular. Thus, upon broaching, the resultant needle blanks would be straight, with either circular or rectangular cross-sections and with points at one or both ends. When inner mandrel 12 has a rectangular cross-section, it is preferable that inner surface 52 of outer member 14 be smooth to facilitate assembly, and the parts are merely slid together rather than "threading" inner mandrel 12 into outer member 14. Straight surgical incision members with points at each end may be particularly useful in surgical stitching instruments that have parallel moving jaw structure capable of passing the needles therebetween. It is also contemplated that square or rectangular wire could be held between the inner mandrel and outer member by providing "V" shaped grooves to hold the wire at an angle. Such a configuration may be desirable to facilitate assembly of the inner mandrel and outer member, or to obtain varied tip configurations relative to the square needle body upon broaching.

Referring now to FIG. 6, once broaches 18 have passed through channels 38 and 52 to cut coil portion 54 into a plurality of individual, double chisel pointed needle blanks, inner mandrel 12 and outer member 14 may be removed from respective mounting fixtures to result in a cartridge type assembly consisting of inner mandrel 12 and outer member 14 containing a plurality of curved, chisel pointed needle blanks 80 contained therein. In order to unload needle blanks 80, inner mandrel 12 is rotated in the direction of arrow A relative to outer member 14. As inner mandrel 12 is rotated a waste portion 82, consisting of straight free end portion 60 and a small part of coil portion 54, will fall off of inner mandrel 12. Continued rotation of inner mandrel 12 will result in needle blanks 80 falling free of threads 24 in succession.

The cartridge assembly, or a similar assembly, may be used to present the chisel pointed ends of the needle blanks to various other stations for further finishing and refining while still being retained within threads 34 and prior to being discharged from the cartridge. Thus, it is possible to reliably deliver pointed needle blanks in proper orientation to be handled for subsequent processing.

Also, while the contemplated broaches 18 used with apparatus 10 have a taper point cutting surface, other cutting faces are contemplated to form various other end characteristics in the curved needle blanks, such as for example, a flat or wedged shaped cutting die which would result in at least one flat end in the needle blank. Thus, where a needle blank is formed with at least one flat end, as the needle blanks are rotated off inner mandrel 12, they may be presented to various finishing stations, such as, for example, a laser drilling station for drilling suture holes, notching apparatus for forming apparatus engagement notches, etc.

Preferably, outer member 14 and inner mandrel 12 have an equal length. Thus, the apparatus 10 is capable of forming a sizable quantity of needle blanks 80 upon passing of broaches 18 therethrough.

Referring now to FIG. 7, there is disclosed an alternate outer cylinder 84 having a plurality of longitudinal channels 86 formed therein and an alternate inner mandrel 88 also having a plurality of longitudinal channels 90 formed therein. As with inner mandrel 12 and outer member 14 described hereinabove, channels 86 and 90 are radially alignable to receive opposed pairs of broaches 18 therein. Alternatively, shallower cutting dies may be used in some of channels 86 and 90 to cut less than half the way through coil portion 54 in order to just notch an edge of outer radial surface 58 and/or inner radial surface 56.

Further, inner mandrel 88 may also be provided with an anchoring slot 92 similar to anchor 34 described hereinabove. As shown, each of the channels, such as for example, channels 86 in outer mandrel 84, may be evenly spaced or assume a variety of predetermined or even random spacing, such as, for example, distances a, b and c between channels 86, and radially aligned channels 90, to thereby form various lengths of curved and pointed surgical needle blanks.

It also is contemplated that after a first broach set has cut the needle blanks with pointed tips, such as chisel points, it may be desirable to longitudinally displace the inner mandrel relative to the outer member so as to cause the needle blanks to rotate slightly between the threads, so that one or more subsequent passes of the same or different broaches will result in more complex tip configurations.

Referring now to FIG. 8, there is shown a curved and double chisel pointed needle blank 80 which includes a curved central body portion 94 formed from round wire stock coil portion 54 and having a chisel point 96 at each end thereof. As best shown in FIG. 9, chisel point 96 includes cut chisel edge 72 described hereinabove and flat chisel surfaces 98, 100 formed in inner and outer radial surfaces 56 and 58, respectively, of curved needle blank 80.

Thus, apparatus 10 is particularly suited for rapidly and efficiently forming a relatively large number of curved and double chisel pointed needle blanks upon a single pass of the broaches and containing the individual needle blanks within a cartridge assembly for subsequent processing, such as, for example, tumbling, polishing, flat or side pressing, forming a more complex curve in the needle body having compound radii of curvature, notching, tapering, drilling for suture holes and the like.

It will be understood that various modifications may be made to the embodiments disclosed herein. For example, and as noted hereinabove, various other cutting/broach configurations, such as, for example, flat edge cutting dies to impart a flat or flush cut, or shallow cutting dies for notching a recess into one or both sides of the needle blank (such as a recess to engage a needle holding blade of a surgical apparatus). Thus, a broach for imparting a substantially rectangular notch pan way into the surface of the needle could be passed through a longitudinal channel on one of the inner mandrel or outer member to form one or more shallow notch(es) in the body of needle blanks 100 to facilitate handling the needle during use, such as engagement of the needle with a suturing apparatus. Further, the inner surface of the outer member and the outer surface of the inner mandrel may assume various other shapes, such as, for example, rectangular to form straight double or single pointed needle blanks. Therefore, the above description should not be construed as limiting, but merely as exemplifications as preferred embodiments. Those skilled in the art will envision other modifications within the scope and spirit of the claims appended hereto.

What is claimed is:

1. An apparatus for forming curved needle blanks from a length of wire comprising:
    a) a mandrel for receipt of a length of wire wrapped around an outer surface thereof;
    b) an outer member having an inner surface defining a cavity therein configured and dimensioned to receive the mandrel wrapped with the length of wire, at least one of the mandrel outer surface and outer member inner surface having at least one longitudinal channel therein;
    c) at least one broach configured for insertion within the at least one longitudinal channel such that a cutting edge of the broach projects out of the channel and engages the length of wire; and
    d) a driver configured for engagement with the broach such that movement of the driver causes the broach to move longitudinally within the at least one longitudinal channel and score an edge of the wire.

2. The apparatus of claim 1 wherein the mandrel is cylindrical.

3. The apparatus of claim 2 wherein the outer surface of the mandrel includes a circumferential wire receiving groove formed therein.

4. The apparatus of claim 3 wherein the wire receiving groove has a semicircular cross-section.

5. The apparatus of claim 3 wherein the wire receiving groove has a rectangular cross-section.

6. The apparatus of claim 3 wherein the wire receiving groove has a V shape.

7. The apparatus of claim 3 wherein the wire receiving groove is formed in even pitch in the outer surface of the mandrel.

8. The apparatus of claim 1 wherein the mandrel includes an anchor groove formed in one end face thereof, the anchor groove being configured to retain a portion of the length of wire.

9. The apparatus of claim 1 wherein the outer member includes a circumferential wire receiving groove formed in the inner surface thereof.

10. The apparatus of claim 1 wherein the broach includes a base portion and a cutting portion.

11. The apparatus of claim 10 wherein the cutting portion has progressively deeper cutting teeth.

12. The apparatus of claim 1 wherein the mandrel and outer member each have a plurality of longitudinal channels, the mandrel channels being alignable with the outer member channels.

13. The apparatus of claim 1 wherein the broach is affixed to the driver.

14. An apparatus for forming pointed curved needle blanks from a length of coiled wire comprising:
   a) a mandrel having a circumferential groove along an outer surface thereof for receipt of a length of coiled wire wrapped therein, and at least two longitudinal channels formed in the outer surface;
   b) an outer member having an inner surface defining a bore dimensioned and configured to receive the wire wrapped mandrel therein, the outer member including at least two longitudinal channels along the inner surface thereof; and
   c) at least one pair of broaches longitudinally alternately movable within the mandrel and outer member channels to form chisel points on the portion of the length of coiled wire engaged thereby.

15. The apparatus of claim 14 wherein the inner surface of the outer member includes a circumferential wire receiving groove formed therein for receipt of the wire wrapped inner mandrel.

16. The apparatus of claim 14 wherein the inner mandrel has an end face defining an anchor slot therein, the anchor slot dimensioned and configured for receipt of a straight free end portion of the length of coiled wire therein.

17. A method of forming needle blanks from a length of wire needle stock comprising:
   a) wrapping a length of wire needle stock around a mandrel;
   b) inserting the wire wrapped mandrel within an outer member; and
   c) alternately moving broaches through alternate longitudinal channels formed in the mandrel and the outer member to cut portions of the wire needle stock into needle blanks.

18. The method of claim 17, wherein the broaches have progressively deeper cutting teeth and cut points in the portions of wire needle stock engaged thereby.

* * * * *